United States Patent [19]

Staver et al.

[11] 4,369,793

[45] Jan. 25, 1983

[54] MEDICAL INSTRUMENTATION ELECTRODE APPARATUS

[76] Inventors: Peter J. Staver, 1624 Detroit St., Lincoln Park, Mich. 48146; Clinton Meyering, 15721 Richmond Ave., Southgate, Mich. 48195

[21] Appl. No.: 179,480

[22] Filed: Aug. 18, 1980

[51] Int. Cl.³ .............................................. A61B 5/04
[52] U.S. Cl. ................................................... 128/643
[58] Field of Search ........................ 128/643, 802, 803

[56] References Cited

U.S. PATENT DOCUMENTS

| 3,862,627 | 1/1975 | Hans, Sr. | 128/643 |
| 3,976,055 | 8/1976 | Monter et al. | 128/643 |
| 4,217,908 | 8/1980 | Staver | 128/643 |

FOREIGN PATENT DOCUMENTS 2208653  4/1973  Fed. Rep. of Germany ...... 128/643

Primary Examiner—Lee S. Cohen
Attorney, Agent, or Firm—Irving M. Weiner; Pamela S. Burt; John L. Shortley

[57] ABSTRACT

A medical instrumentation electrode apparatus for use in connecting wiring from an external medical instrument, such as an electrocardiograph machine, with an area of a patient's skin. The apparatus includes a vacuum bell which is interconnectible with a resilient bulb for partially evacuating same and causing a pliable ring disposed on the open end of the bell to collapse against a patient's skin. In this manner, a disposable contact held in place within the vacuum bell by a core portion of the bell is held in electrical contact with the skin area. The core portion is integrally formed with the vacuum bell and includes an upper protruding end for connection with the resilient bulb, and is further provided with an air communication passage extending between the bulb and the interior of the vacuum bell.

10 Claims, 3 Drawing Figures

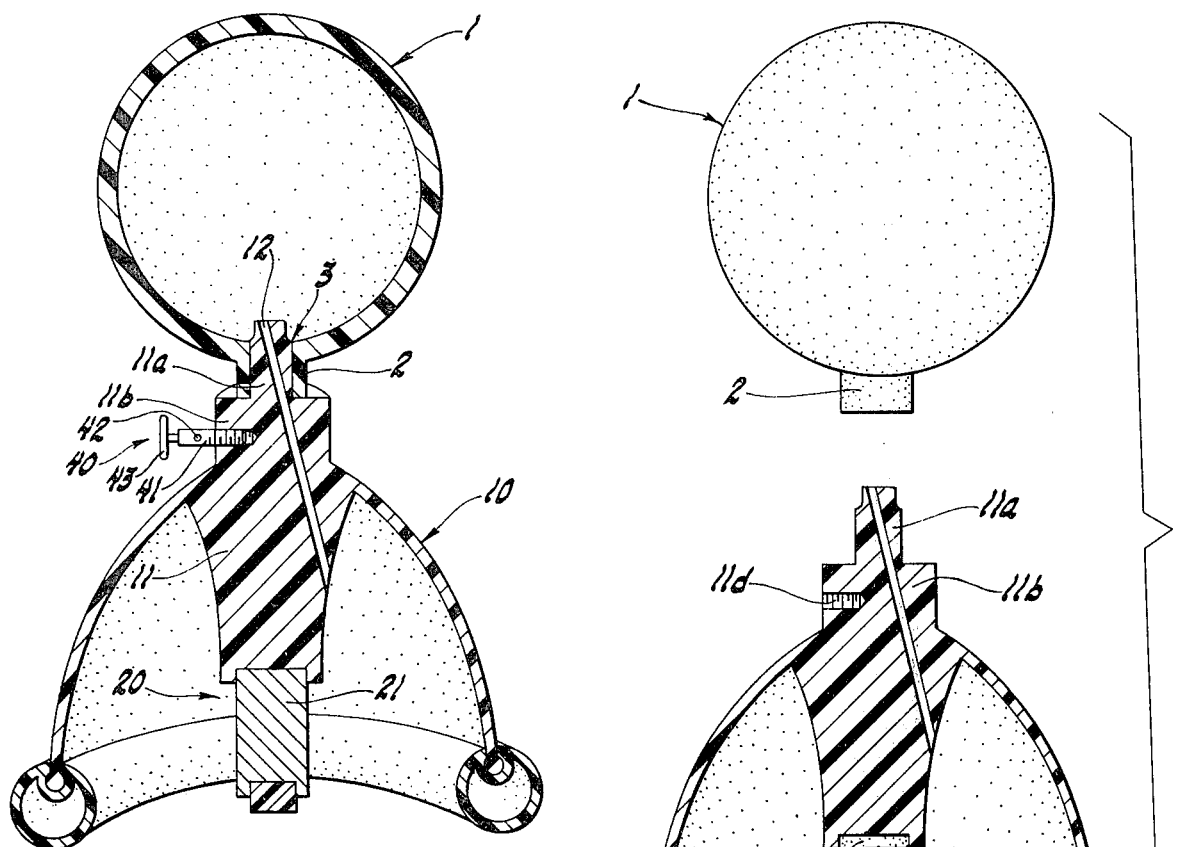
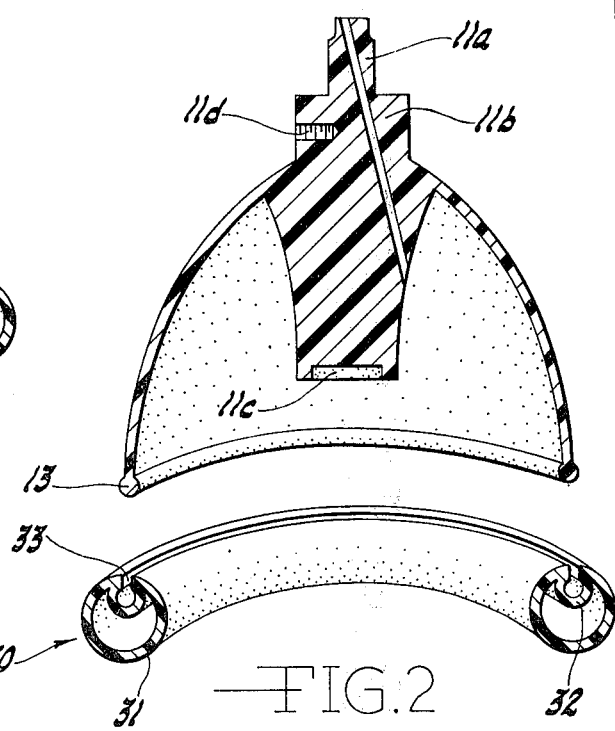
FIG.1
FIG.2
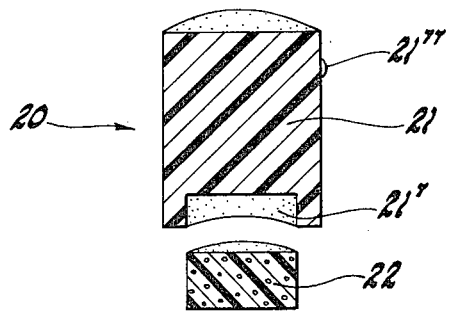
FIG.3

MEDICAL INSTRUMENTATION ELECTRODE APPARATUS

BACKGROUND OF THE INVENTION

1. Field of the Invention

The present invention relates generally to a medical instrumentation electrode apparatus for use on the skin of a subject, the apparatus being used in connection with an external medical instrument such as, for example, an electrocardiograph machine. More particularly, the invention relates to a medical instrumentation electrode apparatus employing disposable contact members, as well as a medical instrumentation electrode kit including various component parts which may be assembled to form the apparatus in accordance with the invention.

2. Description of Relevant Art

In the field of medical electrocardiography, wherein electrical wiring is connected between the surface of a human body and an electrocardiograph (EKG) machine so as to measure and record electrical waveforms emitted by the human heart, various types of apparatus have heretofore been employed for connecting the wiring with the body surface. Common techniques employed for attaching the wires (Vector Leads) to the human body have included the use of flat metallic plates which are taped in position against the skin, or the use of an electrically-conductive suction cup. Both such techniques require the application of a coating of conductive jelly to the skin surface to ensure proper electrical contact.

Illustrative of known attempts to overcome the difficulties associated with attaching electrical wires to the skin surface of either a human or other mammal are: the "SUCTION ELECTRODE" disclosed in U.S. Pat. No. 2,580,628 issued in 1952 to Welsh; the "MASSAGING EQUIPMENT" disclosed in U.S. Pat. No. 2,619,278 issued in 1952 to Ackerman; the "SPRING-LOADED SUCTION CUP-TYPE BIOMEDICAL INSTRUMENTATION ELECTRODE" disclosed in U.S. Pat. No. 3,534,733 issued in 1970 to Phipps; the "ELECTRIC CONTACTOR WITH VENTURI-SUCTION MEANS FOR ORGANIC TISSUE" disclosed in U.S. Pat. No. 3,640,270 issued in 1972 to Hoffmann; the "SUCTION ELECTRODE" disclosed in U.S. Pat. No. 3,783,865 issued in 1974 to Ricketts; the "ELECTRODE AND CONDUCTOR THEREFOR" disclosed in U.S. Pat. No. 3,976,055 issued in 1976 to Monter et al; and the "THERAPEUTICAL/DIAGNOSTIC SUCTION ELECTRODE" disclosed in German Auslegeschrift No. 2,208,653 dated Apr. 5, 1973 in the name of Heyne.

The foregoing apparatus, as well as other known devices, have generally proven deficient with respect to the difficulty involved in employing the apparatus for use, the general complexity of structure, limitations with respect to the types of external apparatus to which the devices may be connected, and other various problems associated therewith.

The present invention provides a medical instrumentation electrode apparatus which effectively overcomes problems associated with prior known devices. The apparatus in accordance with the invention may be employed as a Vector Lead electrode which is adaptable to virtually any currently-employed conventional EKG machine, which eliminates the time-consuming and messy application of conductive gel, and which includes a disposable contact member together with a retaining and support member adapted for re-use.

SUMMARY OF THE INVENTION

The present invention provides a medical instrumentation electrode apparatus including a substantially rigid and hollow vacuum bell and first means for creating a partial vacuum in the bell. The vacuum bell is provided with a core portion formed integrally therewith so as to extend downwardly therewithin, the core portion being fabricated of electrically-conductive material. The core portion has an upper end protruding from the bell for selective interconnection with the first means, and an air communication passage is defined between the bell and the first means. The passage is integrally formed in the core portion of the bell and extends from the upper end of the core portion to a side surface of the core portion disposed within the bell. A contact member including an elongated holder member having an opening defined in the lower end thereof is selectively slidably received and held in an opening provided in the lower end of the core portion such that an electrically-conductive sponge member disposed at least partially within an opening defined in the lower end of the holder member will be disposed proximal to a lower open end of the vacuum bell. Second means are provided for selectively operably connecting the core portion to an external medical instrument such that the sponge member is electrically connected to the medical instrument via the holder member, which is fabricated of electrically-conductive material, and the electrically-conductive core portion of the bell. A substantially hollow resilient ring member is secured coextensively around the periphery of the lower open end of the vacuum bell and is adapted to substantially collapse upon evacuation of the vacuum bell when the ring is disposed adjacent an area of skin, thus bringing the sponge member into contact with an area of skin.

In a preferred embodiment of the invention, the first means comprises a resilient bulb member provided with a neck, and the uppermost portion of the upper protruding end of the vacuum bell core portion is formed so as to closely receive the bulb neck thereon. The second means comprises an electrically-conductive sleeve member secured within the core portion so as to protrude outwardly from the upper protruding end of the core portion, and a screw member is threadedly received within a threaded end portion of the sleeve member. The sleeve member has an aperture disposed therein, and the inner end of the screw member cooperates with the aperture to retain a vector lead wire of the external medical instrument received through the aperture of the sleeve.

It is an object of the invention to provide a medical instrumentation electrode apparatus employing a minimum number of component parts so as to thus facilitate mass production thereof. To this end, because the air communication passage defined between the vacuum bell and the resilient bulb member for evacuating same is integrally formed in the core portion which is in turn integrally formed with the vacuum bell itself, there is thus eliminated any need for an auxiliary member for defining such required passage.

The present invention further contemplates the provision of a medical instrumentation electrode kit wherein various component parts of the apparatus are provided in kit form. Preferably, the kit may include a plurality of the vacuum bells having the integral core portions formed therein; at least one of the resilient bulb members; and a plurality of the contact members, which are disposable.

In accordance with another feature of the invention, the vacuum bell is formed such that the lower open end thereof has a substantially elliptical shape, thus providing a more effective fitting of the bell against the skin area when the bell is being disposed, for example, between the ribs of a patient with a protruding rib cage. Such elliptical shape further facilitates removal and insertion of the disposable contact member within the vacuum bell by enlarging the available space for the user to insert his fingers therein.

Other objects and details of the present invention will become apparent from the following description, when read in conjunction with the accompanying drawings.

BRIEF DESCRIPTION OF THE DRAWINGS

FIG. 1 depicts an electrode apparatus, partially in section, shown in an operative position according to the present invention.

FIG. 2 illustrates, in disassembled form, the vacuum-creating bulb member, the vacuum bell with core portion, and the ring member in accordance with the invention.

FIG. 3 depicts a sectioned view of a disposable contact member including a holder member and electrically-conductive sponge in accordance with the invention.

DETAILED DESCRIPTION OF PREFERRED EMBODIMENTS

With reference to FIG. 1, there is shown the medical instrumentation electrode apparatus of the invention in an assembled, operable condition. The apparatus includes a resilient bulb member 1, which may be fabricated from a conventional rubber or elastomeric material. Bulb 1 has substantially a suction cup structure, and is of a sufficient size to produce a partial vacuum within the vacuum bell 10, as will be described hereinbelow. The bulb 1 includes an integral neck 2 having a cylindrical opening 3 extending coaxially therethrough so as to permit selective interconnection of bulb 1 with vacuum bell 10, as will be described in detail hereinbelow.

The substantially hollow vacuum bell 10 is fabricated of a substantially rigid material and includes a core portion 11 formed integrally therewith. As shown in FIGS. 1 and 2, the core portion 11 extends integrally downwardly within vacuum bell 10 and the portion thereof disposed within vacuum bell 10 is generally conical in shape. Core portion 11 also includes an integral upwardly-protruding end portion including an uppermost end portion 11a which is particularly dimensioned so as to closely receive therearound the neck 2 of bulb 1, and a thickened portion 11b which retains therein a contact assembly (described hereinbelow). It will be understood that the substantially rigid material forming core portion 11 of bell 10 possesses sufficient resiliency to permit ready selective connection of neck 2 of bulb 1 to the core upper end portion 11a while ensuring an airtight seal therebetween.

A substantially straight air communication passage 12 is integrally formed within core portion 11 so as to extend angularly from the uppermost end of core portion 11 to a lower side surface thereof disposed within vacuum bell 10, thus defining an air communication passage between bulb 1 and the interior of vacuum bell 10.

The lower end of core portion 11 is provided with an opening 11c (FIG. 2) which is shaped and dimensioned so as to closely selectively receive and hold therein the upper end of a holder member 21 of a contact member 20, described in detail hereinbelow.

In a preferred embodiment of the invention, the entire vacuum bell 10 including the integral core portion 11 is fabricated of an electrically-conductive material, such as a rigid plastic containing a dispersion of finely-divided conductive particles. In this manner, manufacture of the vacuum bell 10 is greatly facilitated, due to the fact that the entire unit may be lathe-cut or otherwise formed from a single block of material. It will be understood, however, that while it is critical to the functioning of the invention that core portion 11 be formed of electrically-conductive material as will be described hereinbelow, it is not critical that the main outer portion of vacuum bell 10 be electrically-conductive. Accordingly, if desired, vacuum bell 10 may be substantially fabricated of electrically-insulative material with only core portion 11 being formed so as to be electrically-conductive.

The contact member assembly 20, as shown in FIG. 3, comprises a holder member 21 having an opening 21' formed in the lower end thereof to receive and retain therein by means of a friction fit a conductive sponge 22 which preferably is fabricated of a cellular material impregnated with a conductive gel material. The sponge 22 is dimensioned so as to protrude from opening 21' as shown in FIG. 1. The holder member 21 is generally cylindrically shaped, although it will be understood that the particular shape thereof is not critical within the context of the invention, and is fabricated of a conductive material such as conductive graphite plastic containing a dispersion of finely-divided conductive particles. If desired, a non-conductive material plated with a conductive metallic material may alternatively be employed in forming holder member 21. A friction bump 21'' is formed adjacent the upper end of holder 21 on a side surface thereof to ensure retention of holder 21 within opening 11c of core portion 11. The overall construction of contact member 20 permits selective insertion and retention of holder member 21 within opening 11c of core portion 11, or removal therefrom as desired, thus providing contact member 20 with a disposable contact electrode capacity.

As shown in FIG. 2, the bell 10 is provided with a rim 13 integrally formed around the lower open end thereof. A substantially hollow resilient ring member 30, which may preferably be formed of a pliable material, such as latex rubber, includes a relatively thin pliable outer portion 31 which is substantially hollow except for a relatively heavy ring portion 32 formed integrally therein, the ring portions 31 and 32 together defining an upper annular slot 33 adapted to snugly receive therein the rim 13 of vacuum bell 10. If desired, the ring 30 may be formed of a substantially straight section of material of appropriate length such that when the ends thereof are adhesively joined together ring 30 will be properly dimensioned to snap-fit on rim 13. The construction of ring 30, i.e., the pliable outer portion 31, permits collapse thereof against a patient's skin to form an airtight seal therewith when vacuum bell 10 is evacuated, as will be described hereinbelow.

With further reference to FIG. 2, the upper portion 11b of core portion 11 is provided with a threaded bore 11d. Referring to FIG. 1, a contact portion 40 is retained within bore 11d by means of an outer sleeve member 41 formed of electrically-conductive material and threadedly received within bore 11d. A screw 43 is received within the outer end of sleeve member 41, which is internally threaded, and is adapted to retain a Vector Lead wire (not shown) inserted through an aperture 42 in sleeve 41 to thus connect the apparatus with an external medical instrument.

In operation, with reference to FIG. 1, a disposable contact member 20 is secured within vacuum bell 10 by insertion of the holder member 21 into opening 11c of core portion 11. The apparatus is connected to an external medical instrument by inserting a wire or conductor, such as from an EKG machine, through the aperture 42, and tightening screw 43 so as to retain the wire in place. The bulb 1 is squeezed to deform same and force air through passage 12 into vacuum bell 10, and the bell is then positioned such that ring 30 contacts the patient's skin. Upon release of the squeezing hold on bulb 1, air will flow from bell 10 through passage 12 to the interior of bulb 1, thus creating a partial vacuum. Such evacuation will result in the collapse of the pliable ring 30, with the bell 10 being drawn against the patient's skin to form an airtight seal between the bell 10 and the patient's skin. In such condition, the conductive sponge 22 will be drawn into contact with the patient's skin and effectively retained in such position due to the partial vacuum in the surrounding area of bell 10.

The various component portions of the apparatus as above described may be readily assembled and disassembled for replacement of desired components. The ring 30 is readily snapped into position on rim 13 of the bell 10, and may be readily removed therefrom when desired. The disposable contact 20 including electrically-conductive sponge 22, impregnated with conductive jelly so as to eliminate any need for messy application of jelly to the skin, is also easily removable and replaceable.

By way of example, the bell 10 may be approximately one to one and one-half inches in diameter with a dome height of approximately one and one-half inches, while the sponge 22 may be one-half inch or less in diameter.

A primary advantage afforded by the apparatus as described hereinabove resides in the effective minimization of component parts due to the novel structure of vacuum bell 10 with core portion 11. The structure of core portion 11 eliminates the need for any auxiliary connector means between bulb 1 and bell 10, provides means for retaining and holding both the contact portion 40 and the disposable contact member 20, and at the same time provides air communication between bulb 1 and bell 10 via air communication passage 12. Accordingly, because bell 10 with core portion 11 may be easily and inexpensively produced from a single block of material during manufacture, the cost of producing the apparatus is substantially reduced. Further, due to the elimination of auxiliary connecting members, operation of the apparatus is facilitated.

It will be understood from the above description that in an operable position the sponge member 22 will be electrically connected with the external medical instrument (EKG machine) via the electrically-conductive holder member 21, the electrically-conductive core portion 11, and the contact portion 40. The apparatus is universally adaptable to all current types of EKG machines, and due to the novel structure of bell 10 with collapsible ring 30, effective contact of the single contact sponge 22 with the skin is ensured.

Although the pliable feature of ring 30 provides effective conformation thereof to various body contours of a patient, to further enhance such conformation it is contemplated that the lower open end of bell 10 (and consequently ring 30 as well) be formed to have a generally elliptical cross section. Such configuration will facilitate, for example, positioning of the apparatus between the ribs of a patient with a protruding rib cage. Further, such elliptical configuration will facilitate removal and insertion of the disposable contact member 20 within bell 10 by providing more space for the insertion of the user's fingers therein.

With particular reference to FIGS. 2 and 3, the present invention further contemplates that the vector lead apparatus may be provided in the form of an electrode kit. Such a kit would include, for example, a plurality of the vacuum bells 10, (each including a core portion 11 integrally formed therewith), a plurality of the disposable contact members 20, at least one resilient bulb 1, one or more of the rings 30, and one or more of the contact portions 40.

Although there have been described what are at present considered to be the preferred embodiments of the invention, it will be understood that the present invention may be embodied in other specific forms without departing from the spirit or essential characteristics thereof. The present embodiments are therefore to be considered in all respects as illustrative, and not restrictive. The scope of the invention is indicated by the appended claims rather than by the foregoing description.

We claim:

1. A medical instrumentation electrode apparatus, comprising:

a substantially rigid and hollow vacuum bell having a lower open end;

said vacuum bell having a core portion extending downwardly within said vacuum bell toward the open end of said bell, said core portion and said bell constituting a single piece member;

first means for creating a partial vacuum in said vacuum bell;

said core portion having an upper end protruding from said bell for selective interconnection with said first means;

an air communication passage extending between said vacuum bell and said first means through said core portion, said passage extending from said upper protruding end of said core portion to a side surface of said core portion disposed within said bell and being in operative communication with said first means;

said passage being formed within said single piece member;

a contact member including an elongated holder member having an opening defined in the lower end thereof, said holder member being fabricated of substantially electrically-conductive material;

an electrically-conductive sponge member disposed at least partially within said opening of said holder member;

said core portion having an opening defined in the lower end thereof selectively slidably receiving and holding said holder member in a manner such that said sponge member is disposed proximal to a lower open end of said vacuum bell with said holder member being held in said core portion opening;

second means for selectively operably connecting said core portion to an external medical instrument such that said sponge member is electrically connected to said external medical instrument via said holder member and said core portion of said bell;

said core portion being electrically conductive;

a substantially hollow resilient ring member secured to and being co-extensive with the periphery of said lower open end of said vacuum bell; and said ring member, when disposed in contact with an area of human skin, being substantially collapsible upon evacuation of said vacuum bell so as to bring said sponge member into contact with an area of skin.

2. A medical instrumentation electrode apparatus according to claim 1, wherein:

said first means comprises a resilient bulb member, said bulb member being provided with a neck having an opening therein for passage of air therethrough;

the uppermost portion of said upper protruding end of said core portion is formed so as to closely receive said neck thereon;

said air communication passage is substantially straight, and angularly disposed in said core portion;

said bulb member is supported on said upper protruding end of said core portion with said opening in said neck being in communication with said air communication passage.

3. A medical instrumentation electrode apparatus according to claim 2, wherein:

said second means comprises an electrically-conductive sleeve member secured within said core portion so as to protrude outwardly from said upper protruding end of said core portion;

said second means further comprises a screw member threadedly received within a threaded end portion of said sleeve member;

said sleeve member has an aperture disposed therein; and the inner end of said screw member disposed within said sleeve member cooperates with said aperture of said sleeve member to retain a vector lead wire of said external medical instrument received through said aperture of said sleeve.

4. A medical instrumentation electrode apparatus according to claim 1, wherein:

said sponge member is fabricated of a substantially cellular material which is impregnated with an electrically-conductive material; and said ring member is removably secured around a rim portion extending around the periphery of said lower open end of said vacuum bell.

5. A medical instrumentation electrode apparatus according to claim 1, wherein:

said lower open end of said vacuum bell has a substantially elliptical shape.

6. A medical instrumentation electrode apparatus according to claim 1, wherein:

said vacuum bell is fabricated in its entirety of an electrically-conductive material.

7. A medical instrumentation electrode apparatus according to claim 1, wherein:

said holder member of said contact member comprises a substantially cylindrically-shaped solid member.

8. A medical instrumentation electrode kit comprising:

a plurality of substantially rigid and hollow vacuum bells having open ends;

each said vacuum bell having a core portion extending downwardly within said vacuum bell toward the open end of said bell, said core portion and said bell constituting a single piece member;

at least one first means for creating a partial vacuum in individual ones of said vacuum bells;

each said core portion having an upper end protruding from said bell for selective interconnection with said first means;

an air communication passage for flow of air between each said vacuum bell and said first means through said core portion of the bell, said passage extending from said upper protruding end of said core portion to a side surface of said core portion disposed within said bell;

each said passage being formed within the respective single piece member;

said core portion and said first means having mating portions for operatively connecting said air communication passage with said first means;

a plurality of disposable contact members, each said contact member including an elongated holder member having an opening defined in the lower end thereof, said holder member being fabricated of substantially electrically-conductive material;

an electrically-conductive sponge member disposed at least partially within said opening of each said holder member;

each said core portion having an opening defined in the lower end thereof for selectively slidably receiving and holding a holder member of one of said disposable contact members such that said sponge member thereof is disposed proximal to a lower open end of individual ones of said vacuum bells;

second means for selectively operably connecting each said core portion to an external medical instrument such that a said sponge member is electrically connected to a said external medical instrument via a said holder member and a said core portion of the respective said bells when a said sponge member is mounted in a said holder member received in a core portion;

said core portions being electrically conductive;

a substantially hollow resilient ring member secured co-extensively around the periphery of said lower open end of each said vacuum bell; and said ring member, when disposed in contact with an area of human skin, being substantially collapsible upon evacuation of said vacuum bell so as to bring a said sponge member into contact with an area of skin.

9. A medical instrumentation electrode kit according to claim 8, wherein:

said first means comprises a resilient bulb member, said bulb member being provided with a neck;

the uppermost portion of said upper protruding end of each said core portion is formed so as to closely receive said neck thereon; and each said air communication passage is substantially straight, and angularly disposed in each said core portion.

10. A medical instrumentation electrode kit according to claim 9, wherein:

said second means comprises an electrically conductive sleeve member secured within each said core portion so as to protrude outwardly from said upper protruding end of said core portion;

said second means further comprises a screw member threadedly received within a threaded end portion of said sleeve member;

said sponge member is fabricated of a substantially cellular material which is impregnated with an electrically-conductive material; and said ring member is removably secured around a rim portion extending around the periphery of said lower open end of each said vacuum bell.

* * * * *